(12) United States Patent
Hill

(10) Patent No.: US 7,067,141 B2
(45) Date of Patent: Jun. 27, 2006

(54) PESTICIDAL TREATMENT MATERIALS

(75) Inventor: Nigel Lambert Hill, Hertfordshire (GB)

(73) Assignee: A Carey CO LLC, Horsham, PA (US)

( * ) Notice: Subject to any disclaimer, the term of this patent is extended or adjusted under 35 U.S.C. 154(b) by 239 days.

(21) Appl. No.: 10/378,876

(22) Filed: Mar. 5, 2003

(65) Prior Publication Data

US 2003/0130233 A1    Jul. 10, 2003

Related U.S. Application Data

(63) Continuation of application No. 09/680,462, filed on Oct. 6, 2000, now abandoned.

(30) Foreign Application Priority Data

Oct. 6, 1999    (GB) .................................. 9923585.5

(51) Int. Cl.
*A01N 25/34*    (2006.01)
(52) U.S. Cl. ...................... 424/403; 424/405; 424/406; 424/407; 424/409; 424/417; 424/DIG. 10; 514/63; 514/522; 514/531; 514/919

(58) Field of Classification Search ........ 424/403–409, 424/417, DIG. 10; 514/63, 531, 519–522, 514/919, 65–74
See application file for complete search history.

(56) References Cited

U.S. PATENT DOCUMENTS

| 4,103,450 | A | * | 8/1978 | Whitcomb ................... 43/131 |
| 5,898,019 | A | * | 4/1999 | Van Voris et al. .......... 504/360 |
| 6,015,570 | A | * | 1/2000 | Tucci et al. ................. 424/403 |

* cited by examiner

*Primary Examiner*—Neil S. Levy
(74) *Attorney, Agent, or Firm*—Breiner & Breiner, L.L.C.

(57) ABSTRACT

The short term effectiveness of pesticidal articles, for example pesticide impregnated textile covers for use in combating dust mite infestation, is improved by the additional presence of a quick release pesticide thereon, e.g. a wettable powder formulation of the same pesticide as used for impregnation. The invention is of particular value in the area of pyrethroid containing textile covers, e.g. as disclosed in U.S. Pat. No. 5,916,580.

2 Claims, No Drawings

PESTICIDAL TREATMENT MATERIALS

This invention relates to pesticidal treatment materials, particularly to pesticide-impregnated linings and/or coverings for the control of house dust mite populations.

U.S. Pat. No. 5,916,580 discloses the use of preformed netting impregnated with a pyrethroid insecticide for the control of house dust mite populations. This is important in the management of asthma and other allergic conditions where it is well-established that the presence of house dust mite populations, particularly in bedding, gives rise to the presence of a variety of highly antigenic materials, in particular mite faeces. Upholstery and bedding provide a welcome and stable habitat for house dust mites and one where a continuous supply of nutrition in the form of skin particles is relatively assured. United Kingdom Published Application 2330535 discloses similar subject matter.

Tests have shown that using the approach disclosed in U.S. Pat. No. 5,916,580, substantial long-term effective clearance of infestation and protection from reinfestation can be achieved. The reason for this is believed to reside in the fact that by impregnating the netting, the particles of active agent, preferably a synthetic pyrethroid such as permethrin, are held relatively permanently within the netting structure, but gradually released over time enabling them to act against the house dust mites. This mode of action provides long-term treatment, but suffers from the disadvantage that when the netting is first applied, e.g. by fitting a mattress cover or pillow cover around a mattress or pillow, there is little or no immediate effect. The effectiveness builds to a stable level over a period of several weeks, and while this is clearly desirable, no immediate benefit is achieved.

We have now found that this disadvantage can be alleviated by impregnating the netting with the active agent in two different forms, one which is rapidly released and the other of which is substantially slower over an extended period of time.

Thus, according to the first feature of the present invention, there is provided a pesticidal treatment material consisting of a substrate impregnated with a pesticide, the pesticide being present:

in a first concentration in a first form wherein particles of the pesticide are relatively insecurely bound to the structure of the substrate; and in a second concentration in a second form wherein the particles of the pesticide are relatively securely bound to the substrate.

For many applications, the overall concentration of pesticide will be predominantly of the material bound more securely, though applications can be envisaged where the reverse would be true.

Preferably the substrate is a textile netting substrate, for example a polyester netting. The netting may be woven or knitted, e.g. a knitted voile as disclosed in UK Specification 2330535.

It is highly preferable that the pesticide in both rapid release and slow release forms is the same pesticide. This is of assistance in developing commercially saleable products since regulatory authority approval is generally easier achieved for products which include a single active material, the behaviour of which is well-known and documented, rather than for products containing two or more different materials in respect of which there may be little or no knowledge as to whether, used together, there are adverse interactions or implications. Even if there are satisfactory established data available for individual components, regulatory authorities are properly concerned to subject combination treatments to rigorous and often time-consuming scrutiny.

In the particular area of the protection against house dust mite populations, the present invention is simple to put into practice using the preferred pesticides, viz. synthetic pyrethroid compounds. These are well-known and widely available and their use has been established over decades so that their safety and efficacy have been thoroughly explored. Particular mention should be made of permethrin and deltamethrin, both of which have been shown to be highly effective as long-term acaricides against house dust mite populations.

More importantly, from the point of view of practising the present invention, such materials are not only widely commercially available, but available in a number of different formulations which have different physical properties.

In particular, such materials are generally available in two commercial presentations known respectively as wettable powders and emulsifiable concentrates. Both contain the pesticide in question, the former in dry particulate form and the latter in a liquid form.

Wettable powders have been widely used in connection with the provision of a reservoir of pesticide in a derived fixed location, especially on floors and walls of areas of buildings which might otherwise provide sites for pest colonisation. After application—usually by spraying—the pesticide can remain in place for many months, exerting a pesticidal effect on insects, mites or other pests which come into contact with it. As the term implies, the powder is "wettable" and the spray formulation is made by mixing the wettable powder into a quantity of water-based liquid composition, which is then sprayed where needed. On drying off the water, the particles of active agent are present on the surface of the article or structure sprayed, but they are not strongly attached thereto.

As described in U.S. Pat. No. 5,916,580, when emulsifiable concentrates are used, the particles of pesticide tend, because of the formulation of the concentrate, to become much more tightly attached, in the specific case bound to the fine structure of the netting fabric. This has the effect that the particles are gradually released over time to exert their pesticidal action.

Similar results can be achieved by using other formulations which act to impregnate the pesticide material deeply into the structure of the usually textile substrate rather than essentially depositing the pesticide on its surface.

In the manufacture of articles in accordance with the invention, it is desirable to apply the two different forms of pesticide to the substrate at different stages during manufacture. The slow release form of pesticide is conveniently applied to the substrate material in bulk. For example, following its manufacture, textile netting may be passed through an appropriate impregnation bath, dried and subsequently handled in bulk form until it is desired to manufacture the netting into individual articles such as mattress covers. Following the production of those individual articles, the articles themselves can be treated with the quick release formulation and then packaged. This approach avoids the release of large quantities of the pesticide during the inevitable physical handling required when converting bulk material into individual articles. For example, in the case of the manufacture of netting covers, cutting and machine sewing give rise to physical manipulation of the material which would release a quick release formulation unnecessarily and inappropriately, leading not merely to wastage of material, but to a potential build-up of the pesticide material in the workplace where the articles were manufactured. This is avoided by manufacturing the articles first and then applying the quick release formulation just before packaging. Preferably, application is by a method which does not involve much physical manipulation of the articles after application of the quick release form. The preferred system is spray application, in particular because it avoids any risk of reducing the concentration of the slow release form of the pesticide from the article, and because it leaves the quick-release form on the article surface and thus instantly available to exert its pesticidal action once the article is unpacked and put to use.

The following example will serve to illustrate the invention:

EXAMPLE

Bulk polyester netting (knitted, 100% polyester multifilament fibre ex Milliken & Company, Spartansburg S.C.) was taken and passed through an impregnating bath consisting of an emulsifiable concentrate of permethrin (PERMANONE ex AgrEvo Environmental Health, Montvale, N.J.). The process conditions were such as to provide a concentration of permethrin, once the wet netting had been dried, of 550 milligrams per $m^2$. Following impregnation and drying, the now impregnated fabric was rolled up and transported to be made into covers.

Mattress, pillow and duvet covers were manufactured from the netting by conventional processes of cutting and sewing. Individual covers were then sprayed with an aqueous spray formulation made up by mixing a wettable powder formulation of permethrin (ex AgrEvo Environmental Health, Montvale, N.J.) at a rate of 10 Kg of wettable powder per 1000 litres of water. Following spraying, the individual covers were hung up to dry. Following drying, the individual covers were folded and packaged into sealed plastics bags. The concentration of permethrin in the final article was around 600 milligrams per $m^2$ of netting in the final article, of which around 550 milligrams per $m^2$ was derived from the emulsifiable concentrate application to the original netting and the remainder from the spraying and drying process effected on the individual items using the wettable powder formulation.

When such items are put to use, because of the presence of the easily available quick release permethrin, they are immediately effective in reducing house dust mite populations. This effectiveness arises from the quick release formulation, which exerts the predominant pesticidal effect for the first few weeks. Thereafter, the quick release formulation is essentially spent, but pesticidal effectiveness, and accordingly the long term effectiveness of the permethrin-impregnated covers, is then maintained over the next two years by the slow release of the permethrin particles applied from the emulsifiable concentrate.

I claim:

1. A pesticidal treatment article consisting of a netting cover impregnated with a pyrethroid pesticide, in which the pyrethroid pesticide is present in particulate form in and on the netting material in a first form and a second form, wherein said first form consists of pesticides bound to the netting material which provide rapid release of such particles from the netting relative to a rate of release for the second form when the cover is put to use and wherein said second form consists of particles bound more securely to the netting material relative to the particles of the first form in order to provide sustained gradual release of particles of the second form therefrom over a substantial period of time.

2. The article of claim 1 wherein the concentration of pesticide in the first form is less than that of the pesticide in the second form.

* * * * *